United States Patent
Ludlow

(10) Patent No.: US 6,169,600 B1
(45) Date of Patent: Jan. 2, 2001

(54) CYLINDRICAL OBJECT SURFACE INSPECTION SYSTEM

(75) Inventor: Jonathan Ludlow, Lexington, MA (US)

(73) Assignee: Acuity Imaging, LLC, Nashua, NH (US)

(*) Notice: Under 35 U.S.C. 154(b), the term of this patent shall be extended for 0 days.

(21) Appl. No.: 09/197,077

(22) Filed: Nov. 20, 1998

(51) Int. Cl.⁷ .................................................. G01N 21/00
(52) U.S. Cl. ........................................ 356/237.1; 131/905
(58) Field of Search ........................... 356/237.1, 237.2, 356/371, 446; 131/905

(56) References Cited

U.S. PATENT DOCUMENTS

| | | | |
|---|---|---|---|
| 4,034,600 | 7/1977 | Motte | 73/41 |
| 4,047,421 | 9/1977 | Spiers et al. | 73/1 R |
| 4,209,955 | 7/1980 | Seragnoli | 53/54 |
| 4,376,484 | 3/1983 | Seragnoli | 209/535 |
| 4,377,743 | 3/1983 | Bolt et al. | 250/223 R |
| 4,511,045 | 4/1985 | SerAgnoli | 209/863.92 |
| 4,574,646 | 3/1986 | Mattei et al. | 73/863.92 |
| 4,592,470 | 6/1986 | Mattei et al. | 209/535 |
| 4,648,232 | 3/1987 | Brinker et al. | 53/54 |
| 4,976,544 | 12/1990 | Neri | 356/394 |
| 5,000,323 | 3/1991 | Cahill et al. | 209/536 |
| 5,013,905 | 5/1991 | Neri | 250/223 |
| 5,109,236 * | 4/1992 | Watanabe et al. | 356/376 |
| 5,127,737 | 7/1992 | Neri | 356/394 |
| 5,209,249 | 5/1993 | Neri | 131/282 |
| 5,223,915 | 6/1993 | Neri | 356/394 |
| 5,228,462 | 7/1993 | Osmalov et al. | 131/280 |
| 5,287,524 | 2/1994 | Rizzoli et al. | 348/86 |
| 5,365,596 * | 11/1994 | Dante et al. | 382/8 |
| 5,366,096 | 11/1994 | Miller | 209/535 |
| 5,392,359 | 2/1995 | Futamura et al. | 382/8 |
| 5,404,023 | 4/1995 | Neri et al. | 250/572 |
| 5,414,270 | 5/1995 | Henderson et al. | 250/572 |
| 5,432,600 | 7/1995 | Grollimund et al. | 356/237 |
| 5,569,931 | 10/1996 | Ghini et al. | 250/559.45 |
| 5,774,177 * | 6/1998 | Lane | 382/128 |

FOREIGN PATENT DOCUMENTS

| | | | |
|---|---|---|---|
| 0100537 | 2/1984 | (EP) | 19/28 |
| 0136092 | 4/1985 | (EP) | 19/28 |
| 0146800 | 7/1985 | (EP) | 19/30 |
| 0157087 | 10/1985 | (EP) | 19/28 |
| 0166088 | 1/1986 | (EP) | 19/30 |
| 0198282 | 10/1986 | (EP) | 19/28 |
| 0314521 | 5/1989 | (EP) | 9/74 |
| 0338241 | 10/1989 | (EP) | 19/30 |
| 0382466 | 8/1990 | (EP) | 21/88 |
| 0231779 | 8/1991 | (EP) | 19/30 |

(List continued on next page.)

* cited by examiner

Primary Examiner—Richard A. Rosenberger
(74) Attorney, Agent, or Firm—Bourque & Associates, P.A.

(57) ABSTRACT

An inspection system and method for optically inspecting substantially the entire circumference of a cylindrical surface, such as a cigarette is provided. The system includes first and second moveable supports for supporting and transporting the cigarette so that a first side of the cylindrical surface of the cigarette is presented to a first visual inspection apparatus and a second side, which includes at least those portions of the cylindrical surface of the cigarette not included in the first side, is presented to a second visual inspection apparatus. Each visual inspection apparatus includes an illumination source for illuminating the presented side of the cigarette's surface. Each illumination source is configured to direct light onto the cigarette's surface substantially in the direction of the longitudinal axis of the cigarette at a low, acute angle with respect to the longitudinal axis. An image of each presented side of the cigarette is captured using an image capture device, which is preferably a time domain and integration (TDI) camera. The system also includes multiple inspection system processors for processing the captured images.

22 Claims, 11 Drawing Sheets

FOREIGN PATENT DOCUMENTS

| | | | |
|---|---|---|---|
| 0501784 | 9/1992 | (EP) | 15/70 |
| 0518141 | 12/1992 | (EP) | 19/30 |
| 0519595 | 12/1992 | (EP) | 15/70 |
| 0523628 | 1/1993 | (EP) | 5/47 |
| 0316652 | 2/1993 | (EP) | 19/30 |
| 0307661 | 3/1993 | (EP) | 19/30 |
| 0585686 | 8/1993 | (EP) | 5/34 |
| 0582868 | 2/1994 | (EP) | 21/88 |
| 0630586 | 6/1994 | (EP) | 5/34 |
| 0634112 | 7/1994 | (EP) | 5/34 |
| 0615906 | 9/1994 | (EP) | 19/30 |
| 0731024 | 9/1996 | (EP) | 19/30 |
| 5220855 | 2/1977 | (JP) | 11/2 |
| 6119829 | 9/1981 | (JP) | 15/8 |
| 2107178 | 4/1990 | (JP) | 5/34 |
| 2174664 | 7/1990 | (JP) | 5/34 |
| 2193008 | 7/1990 | (JP) | 11/24 |

CYLINDRICAL OBJECT SURFACE INSPECTION SYSTEM

FIELD OF THE INVENTION

This invention relates to a system and method of optically inspecting cylindrical surfaces and more particularly, to a system and method of inspecting cigarettes at high speeds during their manufacture.

BACKGROUND OF THE INVENTION

It is highly desirable to be able to inspect the entire cylindrical surface of cylindrical objects, such as cigarettes during the manufacturing process. Any one of a wide variety of defects may occur in such objects and it is desirable to have an automated system for detecting those defects so that defective objects can be rejected or so that any malfunctioning of the machinery producing those objects can be promptly identified and corrected. In the case of cigarettes, for example, the cylindrical surface may be defective due to a piece of tobacco stem piercing the paper, an imperfection in the way the filter has been joined to the remainder of the cigarette rod, an imperfectly formed side seal which leaves some of the tobacco visible, a discoloration of the cigarette wrapper, due to staining and imperfect ink application, etc.

Although inspection of this kind may take place at any stage in the production of cigarettes, it is most advantageous to perform such inspections after processing of the individual cigarettes is substantially complete. At this point in their fabrication, the individual cigarettes are most easily moved through the cigarette making machinery transverse to their length (side by side).

However, with the cigarettes moving transverse to their length it is much more difficult to image the entire surface of the cigarette. For example, the cylindrical nature of the surface makes uniform illumination of the surface and elimination of shadows difficult. Thus, it may be necessary to inspect the surface piecemeal. However, it is highly desirable to keep the number of inspections to a minimum in order to minimize the need for undue multiplication of complex and expensive inspection system components given the extreme high speed at which cigarettes are moved during the fabrication process.

Additionally, any successful inspection system for products such as cigarettes must be extremely fast in order to keep pace with the high speeds at which such products are typically made. For example, it is now common for a single cigarette making machine to make cigarettes at rates approaching twenty thousand parts per minute. Furthermore, a cigarette inspection system must also be able to inspect cigarettes for relatively small or subtle defects (for example, a hole as small as about 0.5 millimeters in diameter or a minor discoloration of the cigarette wrapper).

Accordingly, it is a principle object of the disclosed invention to provide a cigarette inspection system and method which includes at least one illumination system, which accentuates defects in cigarettes being inspected. It is also an object of the disclosed invention to provide a cigarette inspection system which is capable of inspecting cylindrical surfaces, such as the entire circumference of a cigarette, at very high speeds with a high degree of accuracy. Furthermore, it is an object of the present invention to provide a cigarette inspection system which substantially eliminates the possibility of false defect identification due to airborne contaminants, such as tobacco dust and the like

SUMMARY OF THE INVENTION

These and other objects of the invention are satisfied by providing an inspection system for optically inspecting substantially the entire circumference of a cylindrical surface, which includes a first moveable support for supporting and transporting a cylindrical object, such as a cigarette, so that a first side of a cylindrical surface of the cylindrical object is presented to a first visual inspection apparatus. The inspection system further includes a first illumination source for illuminating the first side of the cylindrical surface when the first side of the cylindrical surface is presented to the first visual inspection apparatus. The first illumination source is configured to direct light onto the cylindrical surface along a longitudinal axis of the cylindrical surface at a low, acute angle with respect to the longitudinal axis.

The inspection system also includes a second moveable support configured to receive the cylindrical object being inspected from the first moveable support and for supporting and transporting the cylindrical object such that a second side of the cylindrical object is presented to a second visual inspection apparatus. The second side of the cylindrical object includes at least all portions of the cylindrical surface of the object which are not inspected in the first side.

Also included in the system is a second illumination source for illuminating the second side of the cylindrical surface when the second side of the surface is presented to the second visual inspection apparatus. The second illumination source, like the first illumination source, is configured to direct light onto the cylindrical surface along the cylindrical axis of the cylindrical object at a low, acute angle with respect to the longitudinal axis.

The first and second visual inspection apparatuses included in the cigarette inspection system each include first and second image capture devices, respectfully. The first and second image capture devices capture first and second images of the cylindrical object. The first image corresponds generally to the first side of the cylindrical object. The second image corresponds generally to the second side of the cylindrical surface.

The disclosed invention further includes a method of inspecting substantially an entire circumference of a cylindrical surface of a cylindrical object. The method begins with supporting the cylindrical object being inspected along its longitudinal axis and transporting the object so that a first side of the cylindrical surface is presented to a first visual inspection apparatus. The first side of the cylindrical surface is then illuminated with an illumination source configured to direct light upon the first side of the cylindrical surface in a longitudinal direction along an illumination axis, which is oriented at a low, acute angle with respect to said longitudinal axis. Once the cylindrical object is illuminated, a first image of the cylindrical object, which corresponds to the first side of the cylindrical surface is captured by a first image capture device. The first image is then analyzed using an image processor to identify defects in the first side of the cylindrical surface.

The cylindrical object is then transported so that a second side of the cylindrical surface of the cylindrical object is presented to a second visual inspection system. The second side of the cylindrical surface includes at least all portions of the cylindrical surface which are not included or imaged in the first side.

The second side of the cylindrical surface is then illuminated with an illumination source which, like the first illumination source, is configured to direct light upon the second side of the cylindrical surface along the illumination axis. A second image of the cylindrical object is then captured with a second image capture device. The second image corresponds to the second side of the cylindrical surface.

Finally, the second image is analyzed using the image processor to identify defects in the second side of the cylindrical surface.

Further features and advantages of the invention will be more apparent from the accompanying drawings and the following detailed description of the preferred embodiments.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Although the principles of the present invention are equally applicable to inspecting the cylindrical surfaces of other types of cylindrical objects, the invention may be understood from the following explanation of its application to inspecting the cylindrical surfaces of substantially finished cigarettes without so limiting the present invention. Similarly, it will be understood that the particular cigarette making machine implementation described below is merely illustrative of one preferred embodiment of this kind and the invention is equally applicable to other cigarette making machine configurations.

If a cigarette is to be inspected for surface defects using an inspection system, then the entire surface area of the cigarette must be visible to the inspection system. Cigarettes are transported through a cigarette maker by means of a series of vacuum wheels that alternately present one side and then the other side of a cigarette to potential inspection locations. Inspection can be effected by acquiring images of the cigarette on adjacent wheels in locations where the cigarette is essentially presented at two different orientations that are substantially 180° apart.

Figure 1:
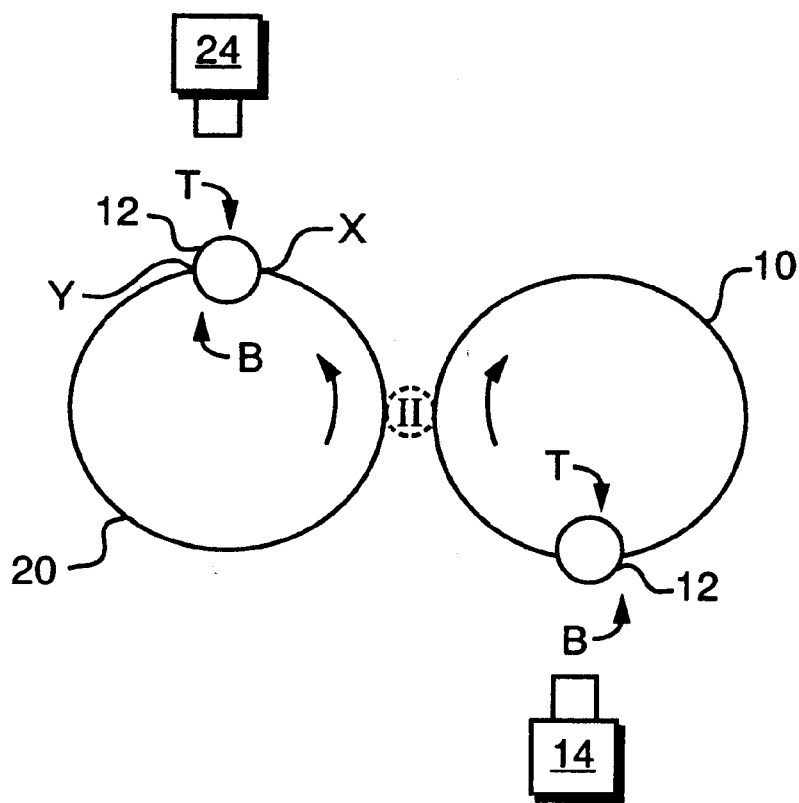
FIG. 1 is a schematic drawing showing how two cameras are used to image both sides of a cigarette passing between two adjacent drums on a cigarette maker in accordance with one embodiment of the present invention.

FIG. 1 shows a simplified diagram of how two image capture devices can be used in conjunction with two adjacent drums on a cigarette maker to capture images of opposite sides of a cigarette passed between the two adjacent drums. In this configuration a cigarette 12 is first held in place by vacuum on rotational drum 10, which, in the embodiment shown in FIG. 1, is rotating in a clockwise direction. When cigarette 12 is presented to image capture device 14, a first side B of the cigarette 12 is visible to the image capture device 14. The image capture device 14 is therefore capable of capturing an image of the first side B of the cylindrical surface of the cigarette.

As first support drum 10 rotates in its clockwise direction, cigarette 12 is moved to a position II, where it is transferred between rotational drum 10 and rotational drum 20. As is well known in the art, vacuum drums with suitable vacuum control systems are used to transport and exchange cigarettes between rotational support drums, such as drums 10 and 20.

In the embodiment of FIG. 1, drum 20 rotates in a counterclockwise direction. As drum 20 rotates, cigarette 12 is presented to a second image capture device 24. However, since the cigarette 12 was exchanged from drum 10 to drum 20, a second side T of cigarette 12 is now visible to be captured by the second image capture device 24.

Figure 2A:
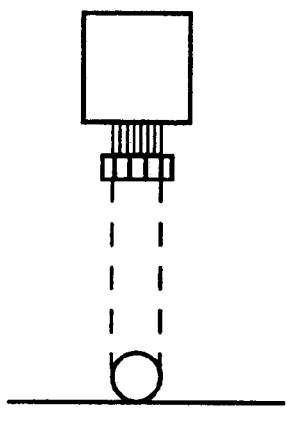
FIG. 2A is a schematic diagram showing a standard camera and lens configuration, which only allows a limited image of a cigarette to be captured.

A potential disadvantage of this otherwise efficient approach is that a defect that is present on the cigarette in either the "three o'clock" X or "nine o'clock" Y position would not normally appear in the images acquired by the first and second image capture devices. This is due to the fact that a standard camera and lens configuration will normally only be able to accurately view the top 160 or so degrees of the cigarette (FIG. 2A).

A number of approaches can be used for cigarette inspection that are aimed at addressing this vision system limitation. These approaches involve implementing optical systems between the image capture devices and the cigarette being inspected that will allow the image capture device to "see" at least 180° of the cigarette.

Figure 2B:
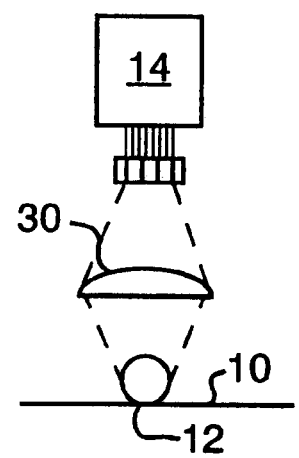
FIG. 2B is a schematic diagram showing a camera with a cylindrical auxiliary lens, which is used to see a wider surface area of a cigarette and greater than 180° the cigarette's cylindrical surface.
Figure 3A:
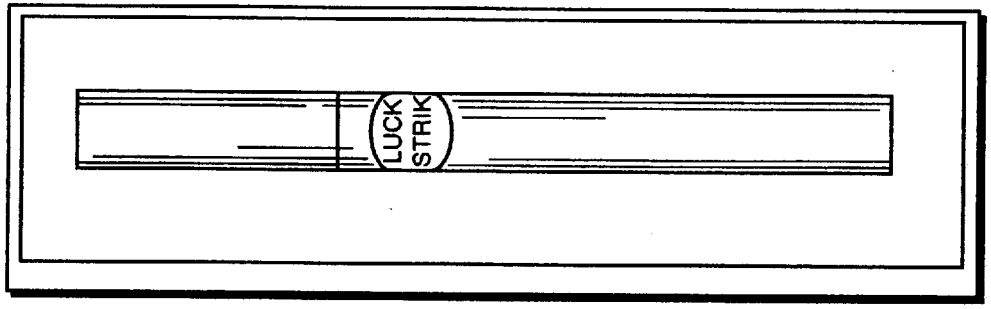
FIG. 3A is an image of a cigarette captured using the standard camera and lens configuration of FIG. 2A.
Figure 3B:
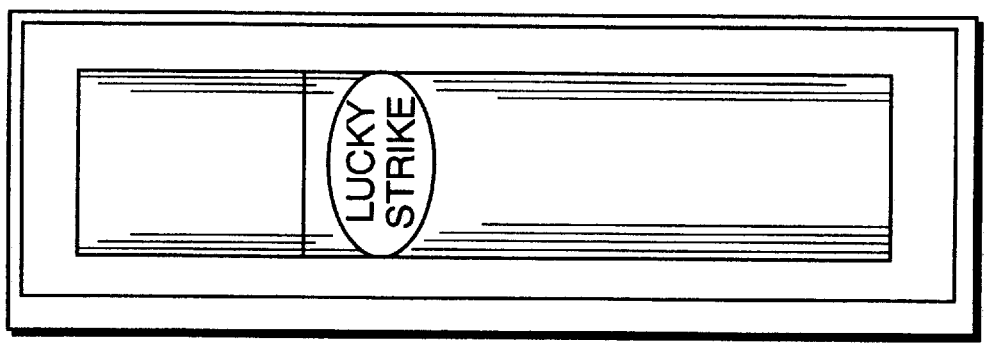
FIG. 3B is a widened image of the same cigarette of FIG. 3A, which is captured using the camera with cylindrical auxiliary lens of FIG. 2B.

FIGS. 2B–7 disclose optical systems which act as image wideners to effectively "stretch" the image being captured. For example, FIG. 2B illustrates and demonstrates a simple implementation that employs a cylindrical lens placed in proximity to the cigarette with the cylindrical axis of the lens aligned parallel to the longitudinal axis of the cigarette. The effect of the cylindrical lens 30 is to stretch the image of the cigarette in the direction normal to the lens axis. Therefore, the resulting image includes a greater proportion of the circumference of the cigarette's surface. As can be seen in FIG. 3A, a standard image of the LUCKY STRIKE® cigarette using a standard camera and lens configuration, such as the one shown in FIG. 2A, results in the partial obscuring of the letters "Y" and "E" since these letters appear close to the edge of the cigarette, substantially corresponding to the 180° position of the cigarette's cylindrical surface. However, when the cylindrical lens 30 is implemented according to FIG. 2B, it is clear that the last two letters of the brand name (Y and E) are visible in the stretched image (FIG. 3B).

Figure 4:
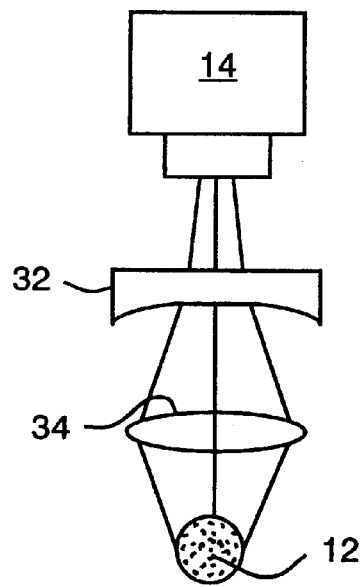
FIG. 4 is a schematic diagram showing the use of a combination of convex and concave cylindrical lenses to provide full coverage of one side of a cigarette being inspected.

This approach is not limited to the use of a simple convex cylindrical lens. Other potentially advantageous optical configurations are shown in FIGS. 4 through 7. For example, FIG. 4 shows the use of a concave cylindrical lens 32 used in combination with a convex cylindrical lens 34 to provide a widened or stretched image of cigarette 12. Convex cylindrical lens 34 stretches the image of the cigarette to include substantially all of the sides of cigarette 12. Concave cylindrical lens 32 then squeezes the image, which includes the sides of the cigarette 12. The squeezed image is then captured by the image capture device 14.

Figure 5:
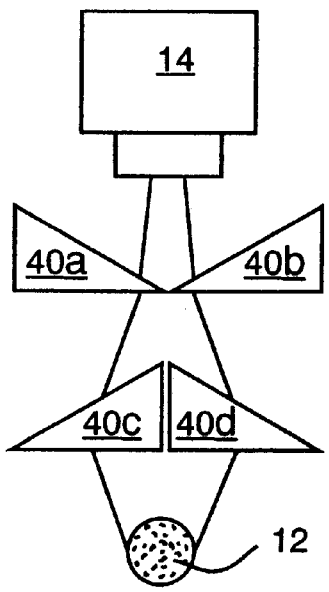
FIG. 5 is a schematic diagram showing the use of a combination of prisms to provide full coverage of one side of a cigarette.

FIG. 5 shows an alternative embodiment which uses a plurality of prisms 40a through 40d to accomplish the desired image widening.

Figure 6:
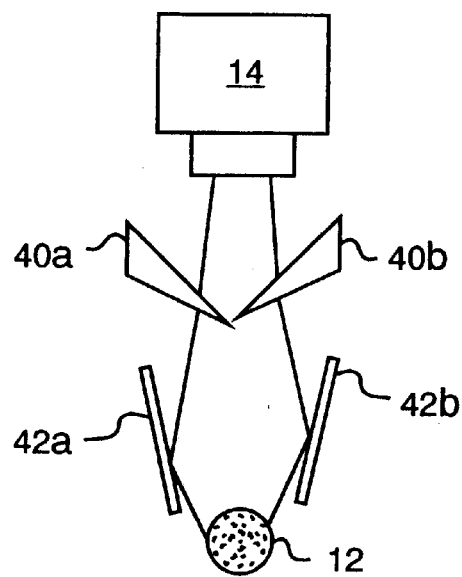
FIG. 6 is a schematic diagram showing the use of a combination of prisms and mirrors to provide full coverage of one side of a cigarette.

FIG. 6 shows an embodiment of an image widener which includes prisms 40a and 40b used in combination with mirrors 42a and 42b to transmit an image of the leading and trailing edge of the cigarette to the image capture device 14.

Figure 7:
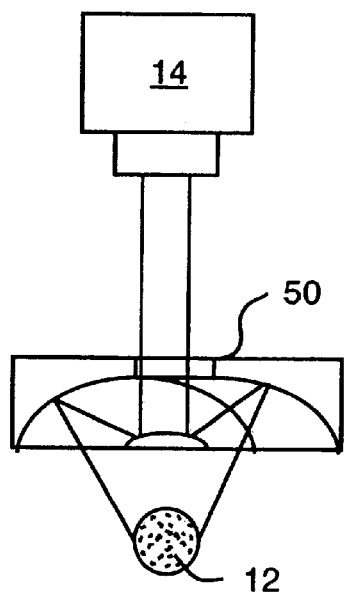
FIG. 7 is a schematic diagram showing the use of reflective optics to provide full coverage of one side of a cigarette.

FIG. 7 shows an even more complex image widener which includes a reflective optics lens 50, which transmits an image of the leading and trailing edge of the cigarette to the image detection device 14.

The capture of images of cigarettes being transported by vacuum wheels in a cigarette maker requires that a number of constraints related to limited access and potential contamination be overcome. The access constraints relate to the relative proximity of the various vacuum wheels included in a typical cigarette maker. For example, there are a number of small areas which will not support the mounting of an image capture device.

Figure 8:
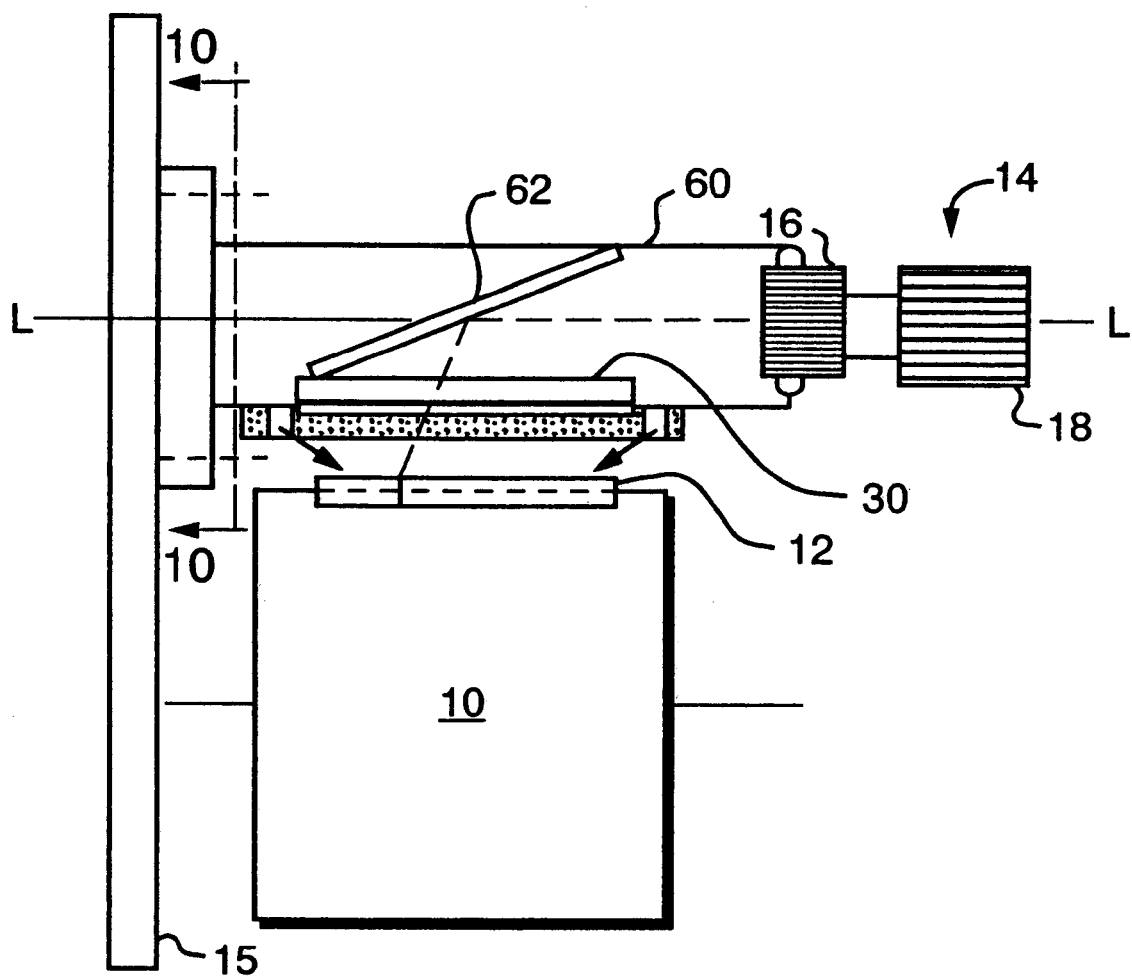
FIG. 8 is a schematic diagram of one configuration of a visual inspection apparatus according to one embodiment of the present invention.

Therefore, it is necessary to include one or more redirection mirrors in one or more visual inspection apparatuses to allow their image capture devices, which are bulky compared to the limited space constraints available, to be mounted in an area large enough to accommodate the image capture devices. One configuration is shown in FIG. 8. In this configuration, an optics enclosure 60 is mounted to a support member 15 of the cigarette maker, such as the back wall of the maker. The optics enclosure 60 includes redirection mirror 62, which redirects the image of cigarette 12 along longitudinal axis L. Mounted at the end of the optics enclosure 60 opposite the end mounted to the cigarette maker support is image capture device 14, which includes lens 16 and camera 18. Also included within optics enclosures 60 may be convex cylindrical lens 30, which acts as an image widener.

Figure 9:
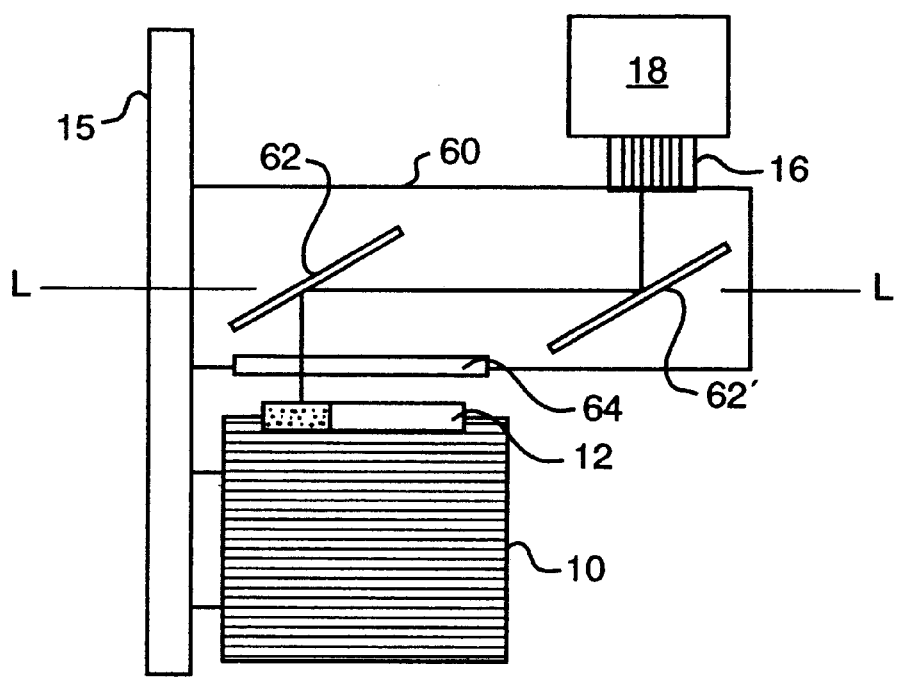
FIG. 9 is a schematic diagram showing an alternate mirror configuration for a visual inspection apparatus according to one embodiment of the present invention.

An alternate embodiment is shown in FIG. 9. In this embodiment, a second redirection lens 62' is included to redirect the image of cigarette 12 away from longitudinal axis L, for example in an upwardly direction, where a vertically mounted camera 18 and lens 16 can capture the image of cigarette 12.

In addition to providing a means of mounting optical and imaging components, the optics enclosure 60 (FIGS. 8 and 9) is intended to provide a means of protecting the optical and imaging components from contamination by the environment that prevails inside a typical cigarette maker. This potential contamination consists primarily of airborne tobacco dust which, if allowed to settle on the optical components or to float into the optical path, would seriously degrade the ability of the inspection system to reliably detect defects. Therefore, the environment inside the optics enclosure 60 will necessarily be protected from dust by either positive ventilation with filtered air or by being effectively sealed.

Figure 10:
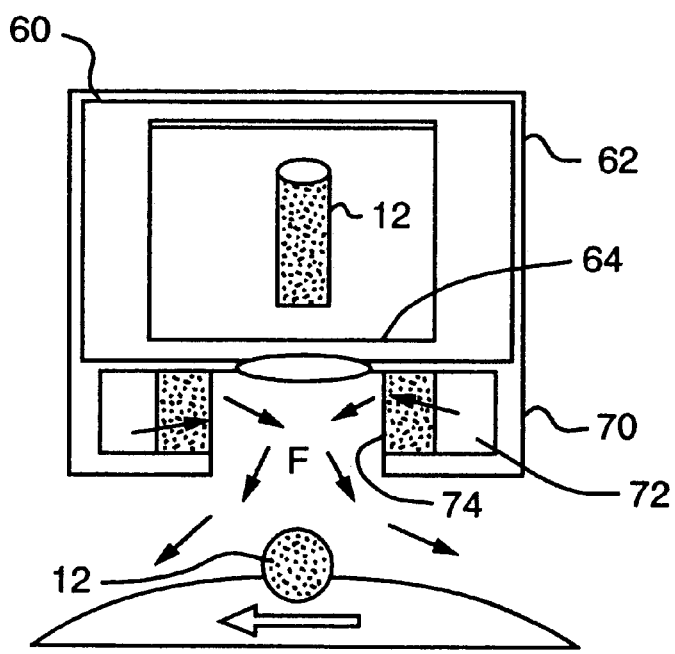
FIG. 10 is a cutaway end view of the visual inspection apparatus taken along lines 10—10 of FIG. 8, showing the flow of air produced by an air curtain.

A sealed optics enclosure will include an optics enclosure window 64 through which the cigarette image is captured. The area around window 64 must also be protected from contamination due to airborne tobacco dust. One means by which this area may be effectively protected is through the use of an air curtain as shown in FIG. 10. Air curtain 70 is configured to provide a constant flow of low velocity air F (supplied at a rate of approximately 10 cubic feet per second) into the region intermediate the optics enclosure window 64 and the cigarette 12 being inspected. Air curtain 70 includes plenum 72 which is provided with a source of filtered air (not shown). The filtered air provided to plenum 72 is introduced into the region intermediate the optics window 64 and cigarette 12 via a porous diffuser 74. In the preferred embodiment, the porous diffuser is made of sintered metal. However, any suitable material is considered an equivalent.

Thus, the filtered air, which is provided at a low velocity into the region intermediate the optics enclosure window 64 and cigarette 12 will aid in preventing airborne tobacco dust from entering the region and aid in the movement of airborne tobacco dust and other contaminants out of this critical region.

The flow of low velocity air in the region intermediate the optics enclosure window and the cigarette being inspected, when combined with a time domain and integration (TDI) camera as the image capture, device provides a number of significant advances over the prior art. A TDI camera is a charge coupled device (CCD) imaging sensor implementation in which an image is electronically "panned" across the sensor S in the manner shown in FIG. 11. Provided the object being imaged, such as cigarette 12, is moved so that it remains precisely in registration with the shifting image, then the image of the object will remain in focus. If, on the other hand, another object, such as an airborne tobacco dust particle, in the image plane moves so that its motion is not in registration with the motion of the image across the sensor, the resulting image of the second object (e.g. the dust particle) will be blurred.

This behavior can be used to greatly reduce the effects of dust or debris on the performance of a cigarette inspection system since dust or debris that is not moving precisely with the cigarette being inspected will be blurred in the resulting image, while defects of similar size, such as pin holes or stem holes will be in sharp focus, and, therefore, will have sharp and distinct edges.

Figure 11:
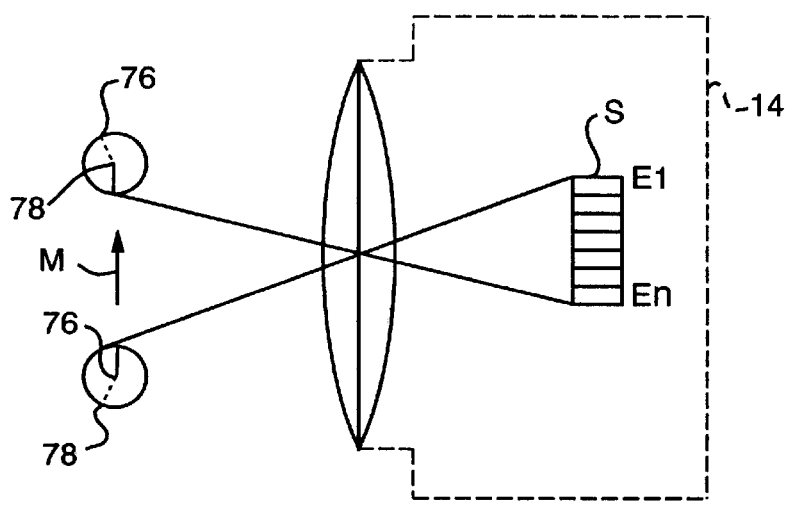
FIG. 11 is a schematic diagram of image data captured by a time domain integration (TDI) camera, showing the operating principle thereof.

Additionally, the use of a TDI camera allows for the capture of an image of a cylindrical object moving past the camera on a drum to include somewhat greater than 180° of the cylindrical surface being imaged. As can be seen in FIG. 11, when cigarette 12 first enters the field of view of TDI camera 14, which occurs at position 1, the portion of the cylindrical surface of the cigarette that is first imaged by a first sensor element, El, of the TDI camera is at approximately the 11:30 position 76 (in terms of a clock face). As the cigarette 12 pans across the field of view of the TDI camera 14, additional sensor elements will image additional portions of the cylindrical surface of cigarette 12 until a final sensor element En images a last portion of the cigarette's cylindrical surface at position 2. As can be seen, at position 2, sensor En images a portion of the cigarette's cylindrical surface corresponding substantially to a 6:30 position 78 (again using a clock face position analogy). Accordingly, the complete image captured by the TDI camera covers substantially between 11:30 and 6:30 positions, which is considerably more than 180 degrees. Thus, a TDI camera provides the image widening or stretching features previously available using optical hardware such as the lens and prism configurations described with respect to FIGS. 3 through 7.

Figure 12A:
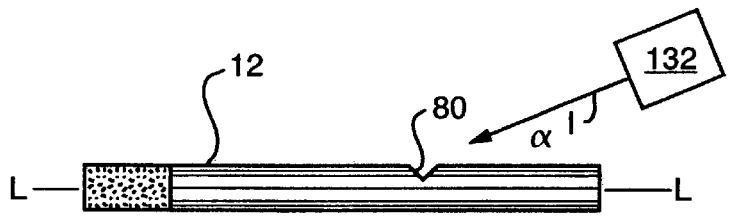
FIG. 12A is a side view of a cigarette, showing the direction of illumination and a wrinkle in the cigarette's surface.
Figure 12B:
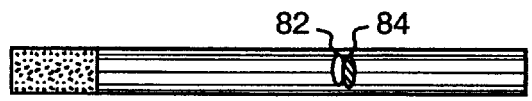
FIG. 12B is a top view of the wrinkled cigarette of FIG. 12A showing the highlights and shadows created by illuminating the wrinkle.

Another feature of the disclosed invention involves the illumination of the cylindrical surface of a cigarette to accentuate the effect of wrinkles and other surface defects. As shown in FIGS. 12A and 12B, by illuminating a cigarette with an illumination source 132 that directs light upon the surface of the cigarette along an illumination axis I, which is oriented substantially along the longitudinal axis of the cigarette at a low, acute angle α with respect to the cigarette's longitudinal axis L, wrinkles 80 or other surface defects are accentuated. This effect is caused by the significant highlights 82 and shadows 84 in the area of the wrinkles 80 produced by the low angle illumination. This illumination configuration also enhances the detectability of holes and other topographic defects. The angle α is preferably in the range of 10 to 30 degrees.

Figure 13:
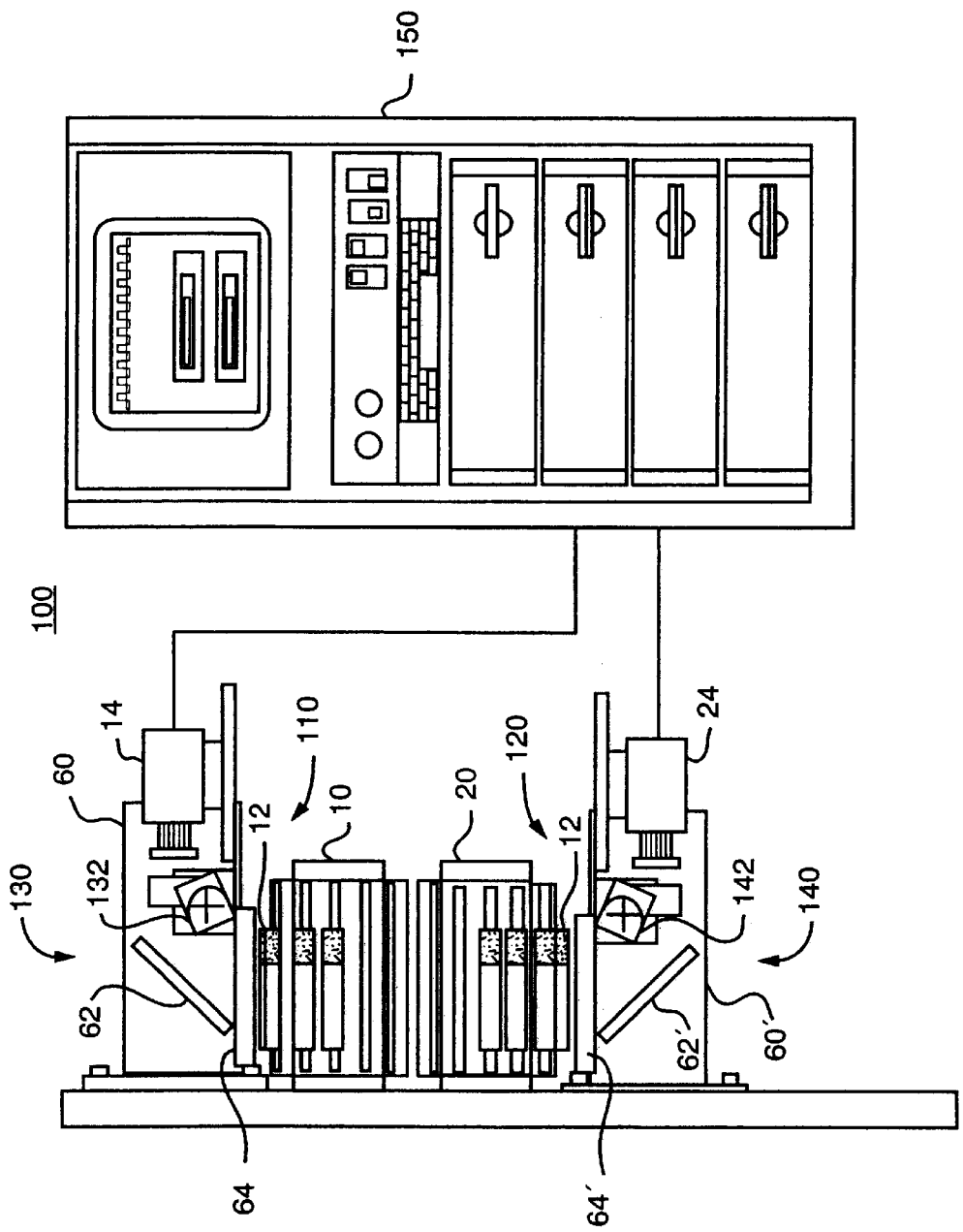
FIG. 13 is a typical inspection system layout showing specific components of the inspection system of the present invention mounted within a cigarette making machine.

FIG. 13 shows a sample cigarette inspection system layout including the major components of a cigarette inspection system. Cigarette inspection system 100 includes first and second visual inspection stations 110 and 120, respectfully.

First visual inspection station 110 includes a first moveable support 10 for supporting and transporting a cylindrical object, such as cigarette 12 so that a first side of cigarette's cylindrical surface is presented to a first visual inspection apparatus 130. When cigarette 12 is presented to the first visual inspection apparatus 130, it is illuminated by a first low angle illumination source 132. Illumination source 132 may comprise either the ends of optical fiber light guides or arrays of high output light emitting diodes (LEDs). In the preferred embodiment, illumination source 132 will comprise multiple illumination sources mounted on either side of camera/optics enclosure 60 and will be located so as to illuminate the cigarette 12 along an illumination axis I, which is oriented in an oblique manner, substantially along the longitudinal axis L of cigarette 12. The illumination source 132 is oriented at a low, acute angle α with respect to the longitudinal axis L of the cigarette in order to accentuate the perceptibility of defects as described above. Optics enclosure 60 provides a mounting support and dust free environment within which an image capture device 14, such as a TDI camera, and a redirection lens 62 are mounted. Although the optical components are sealed within enclosure 60, they view cigarette 12 as it passes visual inspection window 64.

The second inspection station 120 includes a second moveable support 20 for receiving the cylindrical object, such as cigarette 12 from the first moveable support 10 and for supporting and transporting the cigarette 12 so that a second side of the cigarette's cylindrical surface is presented to a second visual inspection apparatus 140.

The second side of the cigarette's cylindrical surface is illuminated by a second illumination source 142, which is substantially identical to the first illumination source 132 described above with respect to the first inspection apparatus 130. The second illumination source 142 illuminates the second side of the cylindrical surface of cigarette 12 when the second side of the cigarette's cylindrical surface is presented to the second visual inspection apparatus 140. Like the first illumination source 132, the second illumination source 142 is configured to direct light onto the cigarette's cylindrical surface along an illumination axis I, which is oriented at a low, acute angle α with respect to the cigarette's longitudinal axis L. The second visual inspection apparatus 140 includes a second image capture device 24, which may substantially identical to the first image capture device 14, although the use of different image capture devices are also contemplated by the invention. Other components of the second visual inspection apparatus 140 are substantially identical to like components found in first inspection apparatus 130 and are indicated on FIG. 13 using like reference numbers.

The images captured by image capture devices 14 and 24 are provided to an image processor 150, which controls the illumination and image capture processes and the processes associated with analyzing the captured images to detect defects in the cylindrical surface of cigarettes.

Figure 14:
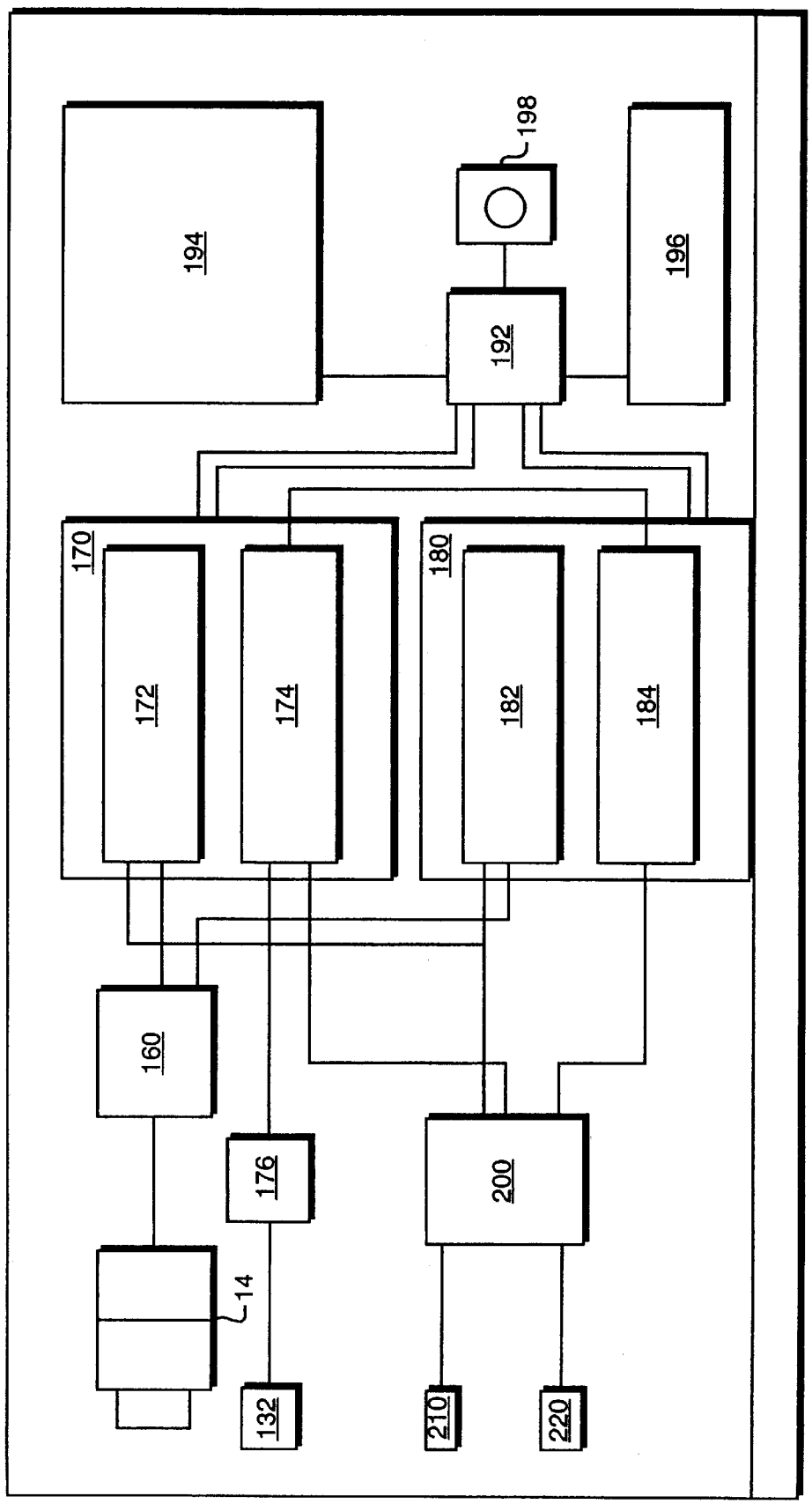
FIG. 14 is a block diagram of one embodiment of a cylindrical surface inspection system constructed in accordance with the teachings of the present invention.

A more detailed block diagram of the components included in each visual inspection apparatus and its associated image processor is shown in FIG. 14. FIG. 14 will be explained with reference to first visual inspection apparatus 130. However, it is understood that the components, which make up second visual inspection apparatus 140 are substantially identical to those described. Common components shared by both visual inspection apparatuses will be indicated in the following description.

An image of the cylindrical surface of an object being inspected is captured by the image capture device 14. In the preferred embodiment, image capture device 14 is a TDI camera as mentioned above. The use of TDI camera provides the capability of imaging moving parts without the need for strobe light sources. It also generates an image in which the effective dust and debris is sensibly eliminated and a larger portion of the circumference of the cigarette is visible (in comparison to a standard area array or line scan camera). A TDI camera will support a multi-platform solution in which high part rates (up to 20,000 cigarettes per minute) can be supported by feeding two image processors from a single camera. TDI cameras are also capable of being adapted to perform part of the image processing during acquisition. For example, the use of a TDI camera with an integral digital system processor (DSP) will allow successful image captures at cigarette manufacturing rates of 10 to 12,000 parts per minute. One TDI camera, which is proven especially useful in practicing the disclosed invention, is the Dalsa Cl-E2 camera.

In one embodiment, a camera multiplexor (MUX) receives the output from TDI camera 14. The camera MUX 160 is used to duplicate the digital signals that represent the image transmitted by the camera. The camera MUX 160 then transmits the captured image to first and second frame grabbers 172 and 182, which are associated with first and second image processors, 170 and 180. First and second frame grabbers, 172 and 182 are preferably Bit Flow frame grabbers, which receive the digital image data captured by TDI camera 14 and which also provide timing and trigger information to TDI camera 14.

The use of the two image processors 170 and 182, effectively doubles the processing speed of the system. Accordingly, camera MUX 160 ensures that the appropriate images are directed to the appropriate image processor. The image processors 170 and 180 include a suitably powerful computer, such as the Power PC6XX family of personal computers. This family of computers provides the enhancement of computing power required to support the high part rates required by a cigarette inspection system. The approach taken by the present invention is to utilize multiple, standard platform computer systems for each inspection station to provide the benefit of modularity and to allow for modifications to tailor a particular inspection station to throughput requirements.

In the preferred embodiment, each image processor also comprises a machine vision system, which forms the basis of the cigarette inspection system. The image processors 170 and 180 may also be equipped with digital input/output (I/O) modules 174 and 184 that may be used for signaling between machines and for generating lighting control and reject signal outputs.

Each visual inspection apparatus also includes lighting controller 176, which is used to adjust light levels as a function of cigarette brand and cigarette maker operating speed. This adjustment may also be required to compensate for aging of light sources if a fiber optic-based illumination scheme is employed. The lighting controller 176 is operated by one I/O module included in one of the image processors.

Each visual inspection apparatus also includes a trigger/reject signal driver 200. The first function of the trigger/reject signal driver 200 is to drive the frame grabber and a part presence trigger 210. The driver 200 also produces a signal that will determine the horizontal and vertical resolution of the images acquired. The signal will be specified in terms of number of encoder counts per revolution.

The requirement for the part presence trigger 210 may be fulfilled by any sensor incorporated into the cigarette maker drum drive that will generate a once per cigarette signal. This signal is used to trigger image acquisition for each cigarette and must be accurately timed with respect to each cigarette to allow the image to be correctly positioned. Thus, the trigger will generate signals that are proportional to machine speed. These signals may also be used to detect when a cigarette maker is up to speed and possibly to control light source intensity levels.

Each inspection apparatus also includes a reject signal driver 220, which provides an appropriate reject signal to the cigarette reject hardware that is generally included in a cigarette manufacturing machine.

In addition to processing and control hardware, the cigarette inspection system also includes a number of user interface items. Although each cigarette inspection system will include two cigarette inspection stations, including duplicate image processors, the inspection stations will share common user interface components. The shared components are selectively connected to the two stations through a selector switch 192. The user interface items include a system display monitor 194, keyboard 196, and pointing device 198.

Figure 15:
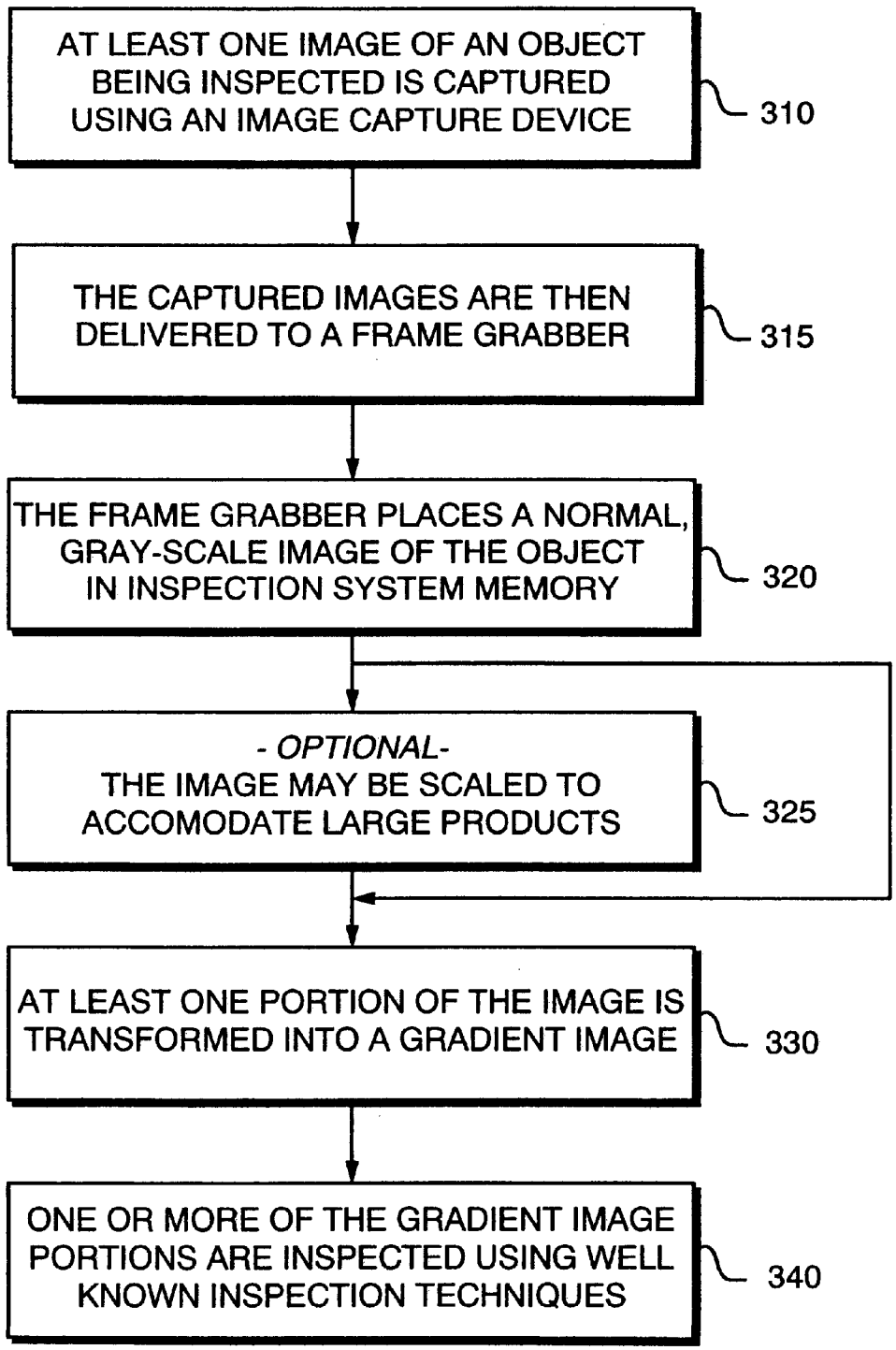
FIG. 15 is a flow chart of an inspection method according to the teachings of the present invention.

In addition to providing appropriate hardware to implement the disclosed cigarette inspection system, a novel inspection method 300, FIG. 15, is accomplished by the image processors included in the system. The image inspection method 300 will be described with respect to one inspection station and one image processor. However, it is understood that the two inspection stations and duplicate image processors utilized by the preferred embodiment of the disclosed cigarette inspection system will allow for the entire cylindrical surface of a cigarette to be properly inspected at typical cigarette manufacturing speeds.

Inspection method 300 begins with an image acquisition step, step 310. Image acquisition includes the capture of an image by the image capture device, such as the TDI camera described above. The TDI camera then delivers the captured image to the frame grabber, step 315, which places a normal, gray-scale image of the cigarette into inspection system memory, step 320. The image is preferably 512×64 pixels in size and may be scaled, step 325, to accommodate large products with allowance for variations in location from cigarette to cigarette.

Once the image is placed into memory and appropriately scaled, if required, image processing and analysis begins. First, at least one portion of the image is transformed using a gradient filter, into a gradient image, step 330. In the preferred embodiment, a vertical edge filter is used, although any suitable gradient filter would be an equivalent. The vertical edge filter may be thought of as a high pass filter, which responds to gradient components (e.g. differences in gray scale values) along the longitudinal axis of the cigarette. Then, one or more of the gradient image portions are analyzed by the image processor, step 340, using well known inspection techniques. A significant advantage of using gradient image portions along with additional inspection techniques is that surfaces can be accurately inspected even when they are being illuminated unevenly. Thus, inspection can be accomplished using less sophisticated, less expensive lighting systems.

Figure 16:
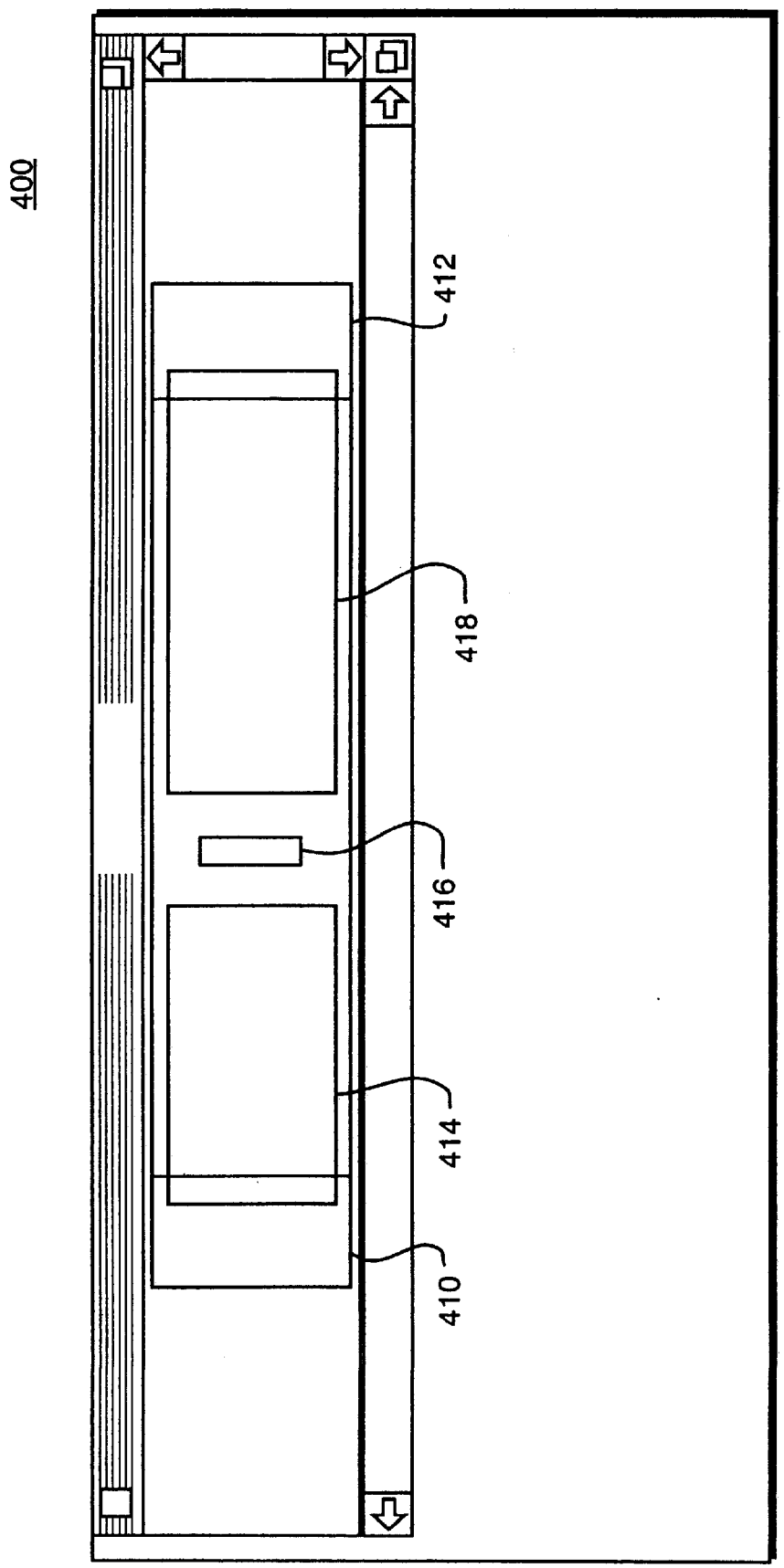
FIG. 16 shows a cigarette gradient image, which is divided into a plurality of regions of interest (ROIs).

In the preferred embodiment, the portion or portions of the cigarette which are subjected to gradient edge filtering are defined based upon a "part program" which will be specific to the product being inspected. FIG. 16 shows a cigarette gradient image 400, which is divided into a plurality of regions of interest (ROI) by one embodiment of a suitable part program. In this embodiment, for example, the part program divides the gradient image of a cigarette being inspected into five (5) regions of interest. The defined regions of interest include: a left end location ROI 410, a right end location ROI 412, a tip inspection ROI 414, a print area inspection ROI 416, and rod inspection ROI 418. Different inspection processes can be applied, independently, to each ROI based on the inspection step being performed for each ROI, including the types of defects applicable. In addition, inspection parameters such as threshold and minimum blob size, which are well known in the art, can be set independently of each of the ROIs defined.

As an example, the five ROIs of FIG. 16 will discussed with respect to the types of inspection steps performed for each. First, the cigarette location can be determined based upon the left end location ROI 410 and the right end location ROI 412. Location determination is performed using connectivity blob analysis. In the two location ROIs, the vertical edges at the tip and rod ends of the cigarette will normally produce well defined, relatively narrow, vertical blobs that precisely define the location, length and angular orientation of the cigarette. Once the cigarette is located, the positions of the inspection ROIs may be adjusted using information from the two location ROIs.

The blobs can also be used for an inspection step in which the angular shape (ratio width) of the end blobs are checked against criteria specified in the part program. This inspection step will be able to detect a variety of defects in tip and rod end formation.

The cigarette inspection process continues by running connectivity analyses on the gradient edge images in each of the three inspection ROIs. Each of these can be supplied with unique parameters to specify threshold, minimum blob size, and other criteria, such as whether the blob can touch the edge of the ROI.

Accordingly, the present invention provides a novel system and method for optically inspecting substantially the entire circumference of a cylindrical surface, which includes first and second visual inspection stations configured to capture images of opposite sides of the cylindrical surface. Each inspection station includes a moveable support for supporting and transporting a cylindrical object, such as a cigarette, so that one side of a cylindrical surface of the cylindrical object is presented to a visual inspection apparatus. Each station also includes an illumination source for illuminating the presented side of the cylindrical surface to the visual inspection apparatus. Each illumination source is configured to direct light onto the cylindrical surface along a longitudinal axis of the cylindrical surface at a low, acute angle with respect to the longitudinal axis.

Each visual inspection apparatus includes an image capture devices for capturing images of the opposite sides of the cylindrical object. The captured images are then analyzed to detect surface defects.

Modifications and substitutions by one of ordinary skill in the art are considered to be within the scope of the present invention which is not to be limited except by the claims which follow.

What is claimed is:

1. An inspection system for optically inspecting substantially an entire circumference of a cylindrical surface of a cylindrical object comprising:

a first movable support for supporting and transporting a cylindrical object so that a first side of a cylindrical surface of said cylindrical object is presented to a first visual inspection apparatus;

a first illumination source for illuminating said first side of said cylindrical surface when said first side of said cylindrical surface is presented to said first visual inspection apparatus, said first illumination source configured to direct light onto said cylindrical surface along a longitudinal axis of said cylindrical surface at a low, acute angle with respect to said longitudinal axis of said cylindrical object being inspected;

a second movable support for receiving said cylindrical object from said first movable support and for supporting and transporting said cylindrical object so that a second side of said cylindrical surface is presented to a second visual inspection apparatus, said second side of said cylindrical surface including at least all portions of said cylindrical surface which are not included in said first side;

a second illumination source for illuminating said second side of said cylindrical surface when said second side of said cylindrical surface is presented to said second visual inspection apparatus, said second illumination source configured to direct light onto said cylindrical surface along said longitudinal axis of said object at a low, acute angle with respect to said longitudinal axis of said cylindrical object; and wherein said first and said second visual inspection apparatus comprise first and second image capture devices for capturing first and second images of said cylindrical object, said first image corresponding to said first side of said cylindrical surface and said second image corresponding to said second side of said cylindrical surface.

2. The inspection system as claimed in claim 1, wherein said first and said second visual inspection apparatus further comprise means to prevent airborne contaminants from settling on the inspection apparatus components.

3. The inspection system as claimed in claim 2, wherein said means to prevent airborne contaminants for setting on said inspection apparatus components comprises a sealed enclosure for housing said components, said enclosure including a window through which images are captured.

4. The inspection system as claimed in claim 3 further comprising an air curtain proximate said window, for providing a low velocity flow of air in the area intermediate said window and said cylindrical object being inspected.

5. The inspection system as claimed in claim 1, wherein at least one of said image capture devices comprises a time domain and integration (TDI) camera.

6. The inspection system as claimed in claim 5 further comprising an image processor, for processing said first and second images to identify visually detectable defects in said first and second sides of said cylindrical surface.

7. The inspection system as claimed in claim 6, wherein said cylindrical object being inspected comprises a cigarette.

8. The inspection system as claimed in claim 1, wherein at least one of said first and second visual inspection apparatuses further comprises an image widener, for allowing at least one of said first and second image capture devices to capture an image of said cylindrical surface that includes greater than one half of said cylindrical surface.

9. The inspection system as claimed in claim 8, wherein said image widener comprises a convex cylindrical lens.

10. The inspection system as claimed in claim 9, wherein said image widener further comprises a concave cylindrical lens in combination with said convex cylindrical lens.

11. The inspection system as claimed in claim 8, wherein said image widener comprises at least one prism.

12. The inspection system as claimed in claim 11, wherein said image widener further comprises at least one mirror in combination with said at least one prism.

13. The inspection system as claimed in claim 8, wherein said image widener comprises a reflective optics lens.

14. The inspection system as claimed in claim 1, wherein at least one of said first and second visual inspection apparatuses further comprises at least one mirror oriented in the field of vision of said image capture device to redirect said image to satisfy space considerations.

15. A method of inspecting substantially an entire circumference of a cylindrical surface of a cylindrical object comprising the steps of:

supporting said object along a longitudinal axis and transporting said object so that a first side of the cylindrical surface is presented to a first visual inspection apparatus;

illuminating said first side of said cylindrical surface with an illumination source configured to direct light upon said first side of the cylindrical surface in a longitudinal direction along an illumination axis which is oriented at a low, acute angle with respect to said longitudinal axis;

capturing a first image of said cylindrical object, said first image corresponding to said first side of said cylindrical surface using a first image capture device, while said first side is illuminated by said first illumination source;

analyzing said first image using an image processor to identify defects in the first side of the cylindrical surface;

transporting said cylindrical object so that a second side of the cylindrical surface of the cylindrical object is presented to a second visual inspection system, said second side of said cylindrical surface including at least all portions of said cylindrical surface which are not included in said first side;

illuminating said second side of said cylindrical surface with an illumination source configured to direct light upon said second side of said cylindrical surface along said illumination axis;

capturing a second image of said cylindrical object with a second image capture device said second image corresponding to said second side of said cylindrical surface while said second side is illumination by said second illumination source; and analyzing said second image using an image processor to identify defects appearing in the second side of the cylindrical surface.

16. The method as claimed in claim 15, wherein at least one of said steps of analyzing said first and said second images comprises transforming at least one portion of at least one of said images into a gradient image portion and analyzing said gradient image portion using an image processor.

17. The method as claimed in claim 16, wherein at least one of said illuminating steps comprises unevenly illuminating said surface.

18. An inspection system for detecting visually detectable defects in cigarettes, said system comprising:

a first visual inspection apparatus comprising a first TDI camera, for capturing a first image of said cigarette, said first image corresponding to a first side of said cigarette;

a first movable support for supporting at least one cigarette along its longitudinal axis and for transporting said cigarette so that the first side of said cigarette is presented to said first visual inspection apparatus;

a first illumination source oriented to direct light substantially along said longitudinal axis of said at least one cigarette at a first, low, acute angle with respect to said longitudinal axis, for illuminating said first side of said cigarette when said first side is presented to said first visual inspection apparatus;

a second visual inspection apparatus comprising a second TDI camera, for capturing a second image of said cigarette, said second image corresponding to a second side of said cigarette;

a second movable support for supporting at least one cigarette along its longitudinal axis and for transporting said cigarette so that the second side of said cigarette is presented to said second visual inspection apparatus; and a second illumination source oriented to direct light substantially along said longitudinal axis of said at least one cigarette at a second, low, acute angle with respect to said longitudinal axis, for illuminating said second side of said cigarette when said second side is presented to said second visual inspection apparatus.

19. The inspection system as claimed in claim 18, wherein said first and second low, acute angles are substantially in the range of 10 to 30 degrees.

20. The inspection system as claimed in claim 18 further comprising an image processor for analyzing said first and second captured images to detect defects in said first and second sides of said cylindrical surface.

21. The inspection system as claimed in claim 20, wherein said image processor comprises a gradient filter to transform said first and second captured images into first and second gradient images.

22. The inspection system as claimed in claim 21, wherein said gradient filter comprises a vertical edge filter.

* * * * *